United States Patent [19]
Miller

[11] Patent Number: 6,156,161
[45] Date of Patent: *Dec. 5, 2000

[54] EXTRACTIVE DISTILLATION PROCESS FOR SEPARATING DIFLUOROMETHANE AND PENTAFLUOROETHANE USING METHYLENE CHLORIDE

[75] Inventor: Ralph Newton Miller, Newark, Del.

[73] Assignee: E. I. du Pont de Nemours and Company, Wilmington, Del.

[ * ] Notice: Under 35 U.S.C. 154(b), the term of this patent shall be extended for 423 days.

[21] Appl. No.: 08/678,564

[22] Filed: Jul. 12, 1996

Related U.S. Application Data

[60] Provisional application No. 60/001,156, Jul. 14, 1995.

[51] Int. Cl.$^7$ ................................. B01D 3/34; C07C 17/38
[52] U.S. Cl. ................................. 203/67; 203/99; 570/178
[58] Field of Search ..................... 203/67, 99; 570/178

[56] References Cited

U.S. PATENT DOCUMENTS

| | | | |
|---|---|---|---|
| 3,732,150 | 5/1973 | Bailey | 203/44 |
| 4,843,181 | 6/1989 | Gumprecht et al. | 570/169 |
| 5,087,329 | 2/1992 | Felix | 203/67 |
| 5,346,595 | 9/1994 | Clemmer et al. | 203/75 |
| 5,367,103 | 11/1994 | Guglielmo et al. | 570/177 |
| 5,421,964 | 6/1995 | Mahler et al. | 203/51 |
| 5,453,551 | 9/1995 | Lacroix et al. | 570/177 |
| 5,585,529 | 12/1996 | Corbin et al. | 570/179 |

FOREIGN PATENT DOCUMENTS

| | | |
|---|---|---|
| WO 92/20640 | 11/1992 | WIPO . |
| WO 95/27689 | 10/1995 | WIPO . |
| WOA95 27689 | 10/1995 | WIPO . |

*Primary Examiner*—Nina Bhat
*Attorney, Agent, or Firm*—James E. Shipley

[57] ABSTRACT

A process is disclosed for removing chloropentafluoroethane (CFC-115) from a mixture comprising CFC-115, difluoromethane (HFC-32), pentafluoroethane (HFC-125), or from mixtures of these compounds, by azeotropic or extractive distillation.

1 Claim, 3 Drawing Sheets

10

EXTRACTIVE DISTILLATION PROCESS FOR SEPARATING DIFLUOROMETHANE AND PENTAFLUOROETHANE USING METHYLENE CHLORIDE

This is a non-provisional patent that is based upon U.S. Provisional Patent Application Ser. No. 60/001,156, filed on Jul. 14, 1995 in the name of Mahler et al. and entitled "Azeotropic Distillation Process For Removing Chloropentafluoroethane From Pentafluoroethane And Other Fluorocarbons"; the disclosure of which is hereby incorporated by reference.

FIELD OF THE INVENTION

The instant invention relates to a process for separating chloropentailuoroethane (CFC-115) and/or hydrofluoric acid (HF) from a mixture comprising chloropentafluoroethane and/or hydrofluoric acid and pentafluoroethane (HFC-125) by distillation processes wherein difluoromethane (HFC-32) is added to, or co-produced with the mixture, and/or in which HFC-32 is used as an extractant in an extractive distillation. The instant invention also relates to a process for coproducing a mixture comprising pentafluoroethane and difluoromethane by contacting a mixture containing pentafluoroethane and difluorornethane precursors with hydrogen fluoride while in the presence of a catalyst, and separating any chloropentafluoroethane and/or hydrogen fluoride from the resultant co-produced mixture by distillation processes.

BACKGROUND OF THE INVENTION

New regulations have been designed to protect the atmospheric ozone layer from possible damage by fully halogenated chlorofluorocarbons, also known as CFC's. Pentafluoroethane (CHF2—CF3 or HFC-125) is a useful non-chlorine containing fluorocarbon that is especially desirable for use as a refrigerant, blowing agent, propellant, fire extinguishing agent, sterilant carrier gas, among other uses.

Pentafluoroethane may be prepared by chlorofluorinating perchloroethylene (perclene or CC12=CC12) to produce a mixture comprising trichlorotrifluoroethane (CF2Cl—CFC12 or CFC-113), dichlorotetrafluoroethane (CF2Cl—CF2Cl or CFC-114) and dichlorotrifluoroethane (CHCl2—CF3 or HCFC-123), thereafter removing trichlorotrifluoroethane, and; fluorinating the remaining mixture to produce a mixture comprising pentafluoroethane (HFC-125), chloropentafluoroethane (CF3—CF2Cl or CFC-115), and smaller amounts of other fluorinated compounds, e.g., hexafluoroethane (CF3—CF3 or FC-116). Such a chlorofluorinating method is described in U.S. Pat. No. 3,755, 477. Various other methods for making pentafluoroethane together with chloropentafluoroethane are known and described, for example, in U.S. Pat. Nos. 3,258,500, 5,334, 787 and 5,399,549, Japanese Patent Application Publication Nos. JP 03/099026, JP 04/029941, European Patent Application Publication No 0 506 525, and World Intellectual Property Organization Publication No. WO 91/05752.

The presence of chloropentafluoroethane (CFC-115) in HFC-125 is considered objectionable, because CFC-115 is a chlorofluorocarbon (CFC) and, therefore, believed capable of harming the ozone layer. However, CFC-115 removal is difficult because the boiling points of pentafluoroethane and chloropentafluoroethane are relatively close, i.e., about −48.5 degrees C and −38.7 degrees C., respectively, and under certain conditions form a known azeotropic or azeotrope-like composition. The above boiling points and azeotropic or azeotrope-like compositions indicate that it would be extremely difficult if not impossible to recover substantially pure pentafluoroethane from such a mixture by conventional distillation. By "conventional distillation" is meant that the relative volatility only of the components of the mixture to be separated is being used to separate them.

The difficulty of separating pentafluoroethane from chloropentafluoroethane is well-recognized, and a number of approaches have been proposed for separating these compounds. U.S. Pat. No. 5,346,595 discloses a method of separating chloropentafluoroethane from pentafluoroethane by a series of distillations performed at different pressures to take advantage of small changes of azeotropic composition with pressure. This process requires multiple distillations and is energy inefficient. U.S. Pat. No. 5,087,329 discloses a method of separating chloropentafluoroethane from pentafluoroethane by extractive distillation with a fluorocarbon extractive agent.

WO 94/02439 discloses a method of removing chlorine-containing impurities from pentafluoroethane by selectively reacting the chlorocarbon with hydrogen. EP 612709 discloses a similar method for removing chloropentafluoroethane from pentafluoroethane by selectively reacting the chlorocarbon with fluorine. Such processes are expensive to perform and may result in some loss of pentafluoroethane by reaction.

WO 94/22793 discloses a method of separating chloropentafluoroethane from pentafluoroethane by contacting the mixture with certain molecular sieves or activated carbons. This process requires the periodic desorption of chloropentafluoroethane from the adsorbent, thus requiring multiple units for continuous operation.

Hydrofluoric acid (HF) is normally a common component of the various fluorination reactions that may be used to produce HFC-125, and it is similarly extremely difficult to remove completely from the HFC-125. Hydrofluoric acid and HFC-125 form an azeotrope that make complete separation of the hydrofluoric acid from the HFC-125 by conventional distillation virtually impossible. The formation of an azeotropic or azeotrope-like composition between HFC-125 and hydrofluoric acid is disclosed in WO96/09271. The presence of HF in HFC-125 is considered objectionable. One method for removing HF from HFC-125 comprises scrubbing the HFC-125 with water. Such a method, however, reduces the value of the scrubbed HF as a raw material in that such cannot be recycled back to the HFC-125 reactor, requires the water wash to be subsequently treated prior to disposition, and; introduces water into the HFC-125 product.

Difluoromethane (CH2F2 or HFC-32) is another desirable non-chlorine containing fluorocarbon that is also valuable as a refrigerant and among other uses. HFC-32 can be formed, for example, by the catalytic fluorination of dichloromethane (HCC-30 or methylene chloride) with HF. HFC-32 is known to form an azeotropic or azeotrope-like composition with CFC-115, and the azeotrope's existence has been disclosed in "Fluorocarbon Refrigerants Handbook", by R. C. Downing, Prentice Hall,1988; U.S. Pat. No. 3,470, 101 to Broadley; and "Pressure-Volume-Temperature Behavior of a Mixture of Difluoromethane and Pentafluoroethane" by Mears et al., Journal of Chemical and Engineering Data, Vol. 13, No. 3, July 1968.

The disclosure of the previously identified patents and publications is hereby incorporated by reference.

CROSS-REFERENCE TO RELATED NON-PROVISIONAL PATENTS AND PATENT APPLICATIONS

Copending and commonly assigned U.S. patent application Ser. No. 08/192,663, filed on Feb. 7, 1994

(corresponding to PCT Publication No. WO 95/21147), and entitled "Process for Separating Pentafluoroethane from a Mixture Comprising Halogenated Hydrocarbons & Chloropentafluoroethane" relates to an extractive distillation process to remove CFC-115 from HFC-125 by using at least one of hydrocarbon, hydrochlorocarbon and chlorocarbon as extractive agents.

Copending and commonly assigned U.S. patent application Ser. Nos. 08/192,664 and 08/378,349, filed respectively on Feb. 7, 1994 and Feb. 1, 1995 (corresponding to PCT Publication No. WO 95/21148), and entitled "Process for Separating Pentafluoroethane from a Mixture Comprising Halogenated Hydrocarbons and Chloropentafluoroethane" relates to an extractive distillation process to remove CFC-115 from HFC-125 by using alcohol-containing extractive agents.

Copending and commonly assigned U.S. patent application Ser. Nos. 08/146,334, filed on Nov. 1, 1993 (corresponding to PCT Publication No. WO 95/12563), and related Ser. No. 08/458,604 filed on Jun. 2, 1995, and entitled "Production of Dihalomethanes Containing Fluorine And Azeotropes Of Dihaloethanes)" relates to a process for producing HFC-32 by contacting HCC-30 (CH2C12) and HF while in the presence of a catalyst.

Copending and commonly assigned U.S. patent application Ser. No. 08/208,256, filed on Mar. 9, 1994 as a continuation in part of Ser. No. 08/055,486, filed on Apr. 30, 1993 (corresponding to PCT Publication No. WO 94/25419), and entitled "Azeotropic and Azeotrope-like Compositions And a Process For Separating HCl and falocarbons" discloses using an azeotrope formed between HFC-125 and CFC-115 to purify HFC-125. U.S. Pat. No. 5,421,964 discloses that HCl is difficult to remove from HFC-125. HCl and HFC-125 exhibit a vapor-liquid equilibrium pinch point that make complete separation of the HFC-125 from the HCl difficult.

Copending and commonly assigned U.S. patent application Ser. No. 08/309,376, filed on Sep. 20, 1994 (corresponding to PCT Publication No. WO 96/09271), and entitled "Purification Process For Hexafluoroethane Products" discloses using an azeotrope formed between HFC-125 and HF.

The disclosure of the aforementioned copending and commonly assigned U.S. Patents, Patent Applications and PCT Publications is hereby incorporated by reference.

SUMMARY OF THE INVENTION

The instant invention solves problems associated with conventional processes by providing methods for purifying HFC-125 by employing an HFC-32/CFC-115 azeotrope for separating or purifying fluorocarbon-containing mixtures. The instant invention further solves problems associated with conventional processes by providing methods for purifying HFC-125 by employing an HFC-32/HFC-125 azeotrope for separating HF and fluorocarboncontaining mixtures, e.g., a process wherein HF is recovered as the bottoms stream and HFC-125/HFC-32 exit as an overhead stream from a distillation column. The instant invention further solves problems associated with conventional distillation processes by employing HFC-32 as an extractant, e.g., a process wherein HFC-125/HFC-32 are recovered as the bottom stream and HCl/CFC-115 exit as an overhead stream from a distillation column. The instant invention further solves problems associated with conventional processes by providing methods for separating HFC-32 and HFC-125, e.g., a process wherein an HFC-125/HFC-32 azeotrope is distilled overhead, leaving a component of the azeotropet (either HFC-125 or HFC-32) which is present in excess of that azeotrope to exit the column bottoms; or, alternatively, a process wherein methylene chloride is used as an extractant in an extractive distillation process for separating HFC-32 and HFC-125, with HFC-32 exiting the extractive distillation column bottoms with the methylene chloride and HFC-125 exiting the extractive distillation column overhead.

The instant invention is capable of producing HFC-125 that contains less than about 2,000 ppm by weight of CFC-115, and typically less than about 500 ppm by weight of CFC-115, e.g., for use as a refrigerant. The instant invention is also capable of producing HFC-125 that contains less than about 2,000 ppm by weight of HF, and typically less than 500 ppm by weight of HF, e.g., for use as a refrigerant. In addition, the instant invention can obtain an "electronic grade" HFC-125 product for use as an etchant in a plasma environment, e.g., HFC-125 that is at least but preferably greater than about 99.99% pure and be virtually free of chlorine containing compounds such as CFC-115. The instant invention also solves problems associated with conventional manufacturing methods by providing a method for co-producing HFC-125 and HFC-32.

One aspect of this invention relates to separating chloropentafluoroethane (CFC-115) from a first mixture comprising CFC-115 and pentafluoroethane (HFC-125) by an azeotropic distillation process comprising the steps of: adding at a minimum an amount of difluoromethane (HFC-32) to the first mixture that is sufficient to form an azeotrope with the CFC-115, thereby creating a second mixture, sparating the CFC-115 from the HFC-125 of the second mixture by azeotropically distilling the low-boiling azeotrope of CFC-115 and HFC-32 overhead in a distillation column, and, recovering a mixture of HFC-125 with HFC-32 substantially free of CFC-115 from the bottom of the distillation column. This process permits removal of CFC-115 from the first mixture with minimal losses of desirable fluorocarbons and with low consumption of HFC-32.

In another aspect of the invention, mixtures comprising HFC-32 and HFC-125 wherein one of the components is present in excess of the azeotropic composition can be separated by a second azeotropic distillation by removing a low-boiling azeotrope of HFC-125 and HFC-32 overhead from a distillation column, and recovering the HFC-125 or HFC-32 in excess of the azeotropic composition from the bottoms stream of the column. If desired, azeotropic compositions of HFC-125 and HFC-32 can be separated by distillation at a pressure and temperature which is different than that corresponding to the azeotropic composition in order to take advantage of the shift in azeotropic composition under these conditions.

HFC-125 that is substantially free of CFC-115 can be produced in a process comprising contacting an HFC-125 precursor and an HFC-32 precursor with HF optionally over a catalyst to produce a mixture comprising HFC-125 and HFC-32, removing impurities other than CFC-115 from the mixture by distillation or other processes, separating the CFC-115 from the mixture comprising HFC-125 and HFC-32 by azeotropically distilling the low-boiling azeotrope of CFC-115 and HFC-32 overhead in a distillation column, and, recovering a mixture of HFC-125 with HFC-32 substantially free of CFC-115 from the bottom of the distillation column.

Further, HFC-125 that is substantially free of HF can be produced in a process comprising contacting an HFC-125 precursor and an HFC-32 precursor with HF optionally over a catalyst to produce a mixture comprising HFC-125 and HFC-32, removing impurities other than HF from the mixture by distillation or other processes, separating the HF from the mixture comprising HF, HFC-125 and HFC-32 by azeotropically distilling the low-boiling azeotrope of HFC-125 and HFC-32 overhead in a distillation column, producing a HFC-125 and HFC-32 stream substantially free of HF, and, recovering the HF from the bottom of the distillation column.

By an "HFC-125 precursor" or "HFC-32 precursor", it is meant any halocarbon which can be contacted with HF to produce HFC-125 or HFC-32. For example, HFC-32 and HFC-125 can be co-produced by contacting a mixture comprising a HFC-32 precursor such as methylene chloride (HCC-30 or CH2C12) and a HFC-125 precursor such as HCFC-123 (dichlorotrifluoroethane) and/or HCFC-124 (chlorotetrafluoroethane) with HF in the presence of a catalyst, e.g., CrC13 on a carbon support or Cr2O3. The following equations illustrate suitable processes for co-producing HFC-32 and HFC-125:

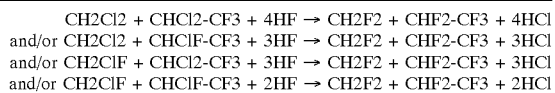

CH2Cl2 + CHCl2-CF3 + 4HF → CH2F2 + CHF2-CF3 + 4HCl
and/or CH2Cl2 + CHClF-CF3 + 3HF → CH2F2 + CHF2-CF3 + 3HCl
and/or CH2ClF + CHCl2-CF3 + 3HF → CH2F2 + CHF2-CF3 + 3HCl
and/or CH2ClF + CHClF-CF3 + 2HF → CH2F2 + CHF2-CF3 + 2HCl The reaction product contains predominant quantities of HFC-32 and HFC-125 along with one or more of the following: HCFC-31 hlorofluoromethane), HCC-30 (dichloromethane or methylene chloride), CFC-114a (dichlorotetrafluoroethane), CFC-115 (chloropentafluoroethane), HCFC-124 (chlorotetrafluoroethane), HCFC-133a (chlorotrifluoroethane), HF (hydrogen fluoride), HCl (hydrogen chloride), among others. Impurities other than CFC-115 and hydrogen fluoride can be efficiently removed from the resulting HFC-125 containing products by conventional distillation or other processes known by one skilled in the art. The CFC-115 and/or the hydrogen fluoride can be removed from the HFC-125 containing products by employing the inventive distillation processes. The ability to produce blends of HFC-32 with HFC-125, and blends of these with other ingredients, utilizing the instant invention is particularly desirable since such blends are useful commercially, e.g., as a refrigerant.

In another aspect, the process of this invention comprises separating HF from a first mixture comprising HF and pentafluoroethane (HFC-125) by an azeotropic distillation process comprises the steps of: adding at a minimum an amount of difluoromethane (HFC-32) to the first mixture that is sufficient to form an HFC-125/HFC-32 azeotrope with the HFC-125, thereby creating a second mixture, separating the HF from the HFC-125 of the second mixture by azeotropically distilling the low-boiling azeotrope or azeotrope-like composition of HFC-125 and HFC-32 overhead in a distillation column, and, recovering the HF from the bottom of the distillation column.

In yet another aspect of this invention, in cases wherein HFC-125 and CFC-115 are distilled in the presence of HCl, we have found that HFC-32 can function as an extractant in an extractive distillation process for separating HFC-125 and CFC-115. This process permits CFC-115 and HCl to exit overhead from the distillation column, while allowing HFC-32 and HFC-125 to exit the column bottoms.

In a further aspect of this invention, methylene chloride can be employed as an extractant in an extractive distillation for separating HFC-32 and HFC-125. This process permits HFC-125 to exit overhead from the distillation column, while allowing methylene chloride and HFC-32 to exit the column bottoms.

DETAILED DESCRIPTION

Figure 1:
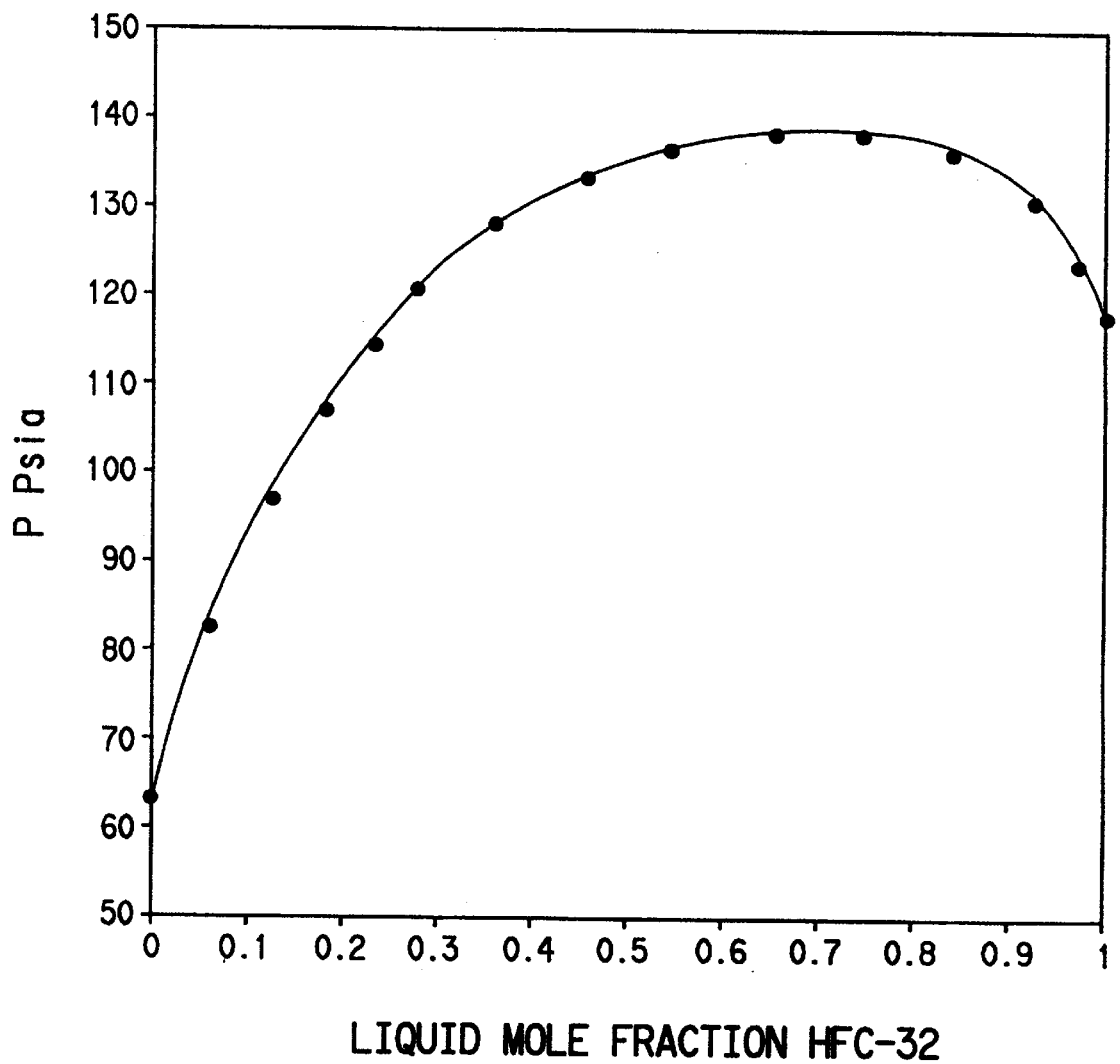
FIG. 1 is a graphical representation at 0° C. of an azeotropic and azeotrope-like composition formed between HFC-32 and CFC-115.

The pentafluoroethane (HFC-125) and chloropentafluoroethane (CFC-115) which are the primary constituents of a first mixture, in their separated and pure state have boiling points, respectively, of about −48.5 and −38.7 degrees C. The relative volatility at atmospheric pressure of FIFC-125/Cl,C-115 was found to be nearly 1.0 as 100% purity of HFC-125 was approached. These data indicate that using conventional distillation processes will not result in the separation of a substantially pure compound.

To determine the relative volatility of HFC-125 and CFC-115 the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126; the entire disclosure of which is hereby incorporated by reference.

These measurements can be correlated to equilibrium vapor and liquid compositions in the cell by using an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references is hereby incorporated by reference.

The behavior of hydrogen fluoride (HF) in such systems may also be calculated by using an appropriate hydrogen fluoride association model in conjunction with the aforementioned methods as described by W. Schotte, Ind.Eng.Chem.Process Des.Dev. 1980, pp. 432–439; the entire disclosure of which is hereby incorporated by reference.

The result of PTx measurements and the above series of calculations for a binary mixture containing HFC-125 and CFC-115 are summarized in Tables 1 through 3, giving results for −25 degrees C., 0 degrees C. and 25 degrees C. Similar measurements were obtained and similar calculations were performed for the other binary compounds of the mixtures in the invention.

Without wishing to be bound by any theory or explanation, it is believed that the NRTL equation can sufficiently predict whether or not HFC-125 and CFC-115 and/or the following other mixtures behave in an ideal manner, and can sufficiently predict the relative volatilities of the components in such mixtures.

TABLE 1

Vapor-Liquid Measurements on the HFC-125/CFC-115 System at −25 deg. C.

| Mole %, CFC-115 | | | Pressure | Relative Volatility |
|---|---|---|---|---|
| Charge | Liquid | Vapor | Meas. (psia) | HFC-125/CFC-115 |
| 17.67 | 17.72 | 15.84 | 40.75 | 1.144 |
| 13.48 | 13.51 | 12.38 | 40.75 | 1.105 |
| 10.40 | 10.42 | 9.74 | 40.95 | 1.078 |
| 7.40 | 7.42 | 7.08 | 41.10 | 1.052 |

TABLE 2

Vapor-Liquid Measurements on the HFC-125/CFC-115 System at 0 deg. C.

| Mole %, CFC-115 | | | Pressure | Relative Volatility |
|---|---|---|---|---|
| Charge | Liquid | Vapor | Meas. (psia) | HFC-125/CFC-115 |
| 17.67 | 17.78 | 15.92 | 96.95 | 1.142 |
| 13.48 | 13.55 | 12.37 | 97.20 | 1.110 |
| 10.40 | 10.45 | 9.69 | 98.00 | 1.087 |
| 7.40 | 7.43 | 7.00 | 98.00 | 1.066 |

TABLE 3

Vapor-Liquid Measurements on the HFC-125/CFC-115 System at 25 deg. C.

| Mole %, CFC-115 | | | Pressure | Relative Volatility |
|---|---|---|---|---|
| Charge | Liquid | Vapor | Meas. (psia) | HFC-125/CFC-115 |
| 17.67 | 17.87 | 16.36 | 198.60 | 1.113 |
| 13.48 | 13.61 | 12.65 | 200.25 | 1.087 |
| 10.40 | 10.49 | 9.88 | 200.75 | 1.069 |
| 7.40 | 7.45 | 7.11 | 201.00 | 1.052 |

The "Charge" column refers to the concentration of CFC-115 that is in a mixture of HFC-125 and CFC-115 that was introduced into the PTx cell. The "Relative Volatility" and the "Mole % CFC-115" in the Vapor and Liquid were those calculated from the measured pressures at the indicated temperature.

While the relative volatility of CFC-115 in comparison to HFC-125 at some relatively low concentrations is sufficient to permit separating CFC-115 by using conventional distillation methods, the relative volatility approaches nearly 1.0 as 100% purity of HFC-125 is approached. A relative volatility approaching 1.0 would render removal of low concentrations of CFC-115 from HFC-125 difficult if not impossible, e.g., conventional distillation would require using large and expensive distillation columns.

Finding the type of compounds which form azeotropic or azeotrope-like compositions, and finding the pair of compounds which specifically will form the lowest-boiling azeotrope at a particular temperature and/or pressure cannot be predicted, but must be identified by experiment (i.e., by measuring binary vapor-liquid equilibria data). Literature values by different investigators on the boiling points or vapor pressures of the above compounds and/or azeotropes at a variety of conditions may not provide consistent information for establishing which compounds or azeotropic or azeotrope-like compositions are lowest boiling under a single set of conditions, since the azeotropic or azeotrope-like compositions frequently change with pressure and temperature.

By "azeotrope" or "azeotropic" composition is meant a constant-boiling liquid admixture of two or more substances that behaves as a single substance. One way to characterize an azeotrope or azeotropic composition or mixture is that the vapor produced by partial evaporation or distillation of the liquid has the same composition as the liquid from which it was evaporated or distilled, e.g., the admixture distills/refluxes without compositional change. Constant boiling compositions are characterized as azeotropic because they exhibit either a maximum or minimum boiling point, as compared with that of the non-azeotropic mixture of the same components. A azeotropic composition can also be characterized as the maximum or minimum vapor pressure for a mixture at a given temperature when plotted as a function of mole fraction.

By "azeotrope-like" composition is meant a constant boiling, or substantially constant boiling admixture of two or more substances that behaves as a single substance. One way to characterize an azeotrope-like composition is that the vapor produced by partial evaporation or distillation of the liquid has substantially the same composition as the liquid from which it was evaporated or distilled, e.g., the admixture distills/refluxes without substantial compositional change. An azeotrope-like composition can also be characterized by the area, which is shown by plotting vapor pressure at a given temperature as a function of mole fraction, that is adjacent to the maximum or minimum vapor pressure.

Typically, a composition is azeotrope-like, if, after 50 weight percent of the composition is removed such as by evaporation or boiling off, the change between the original composition and the composition remaining is less than about 6%, and normally less than about 3% relative to the original composition.

By "effective amount" is intended to refer to the amount of each component of the inventive compositions which, when combined, results in the formation of an azeotropic or azeotrope-like composition. This definition includes the amount of each component, which amounts may vary depending on the pressure applied to the composition so long as the azeotropic or azeotropic-like compositions continue to exist at the different pressures, but with possible different boiling points. Effective amount also includes the amounts, such as may be expressed in weight percentages, of each component of the compositions of the instant invention which form azeotropic or azeotrope-like compositions at temperatures or pressures other than as described herein. Therefore, included in this invention are azeotropic or azeotrope-like compositions consisting essentially of effective amounts of at least one of CFC-115 and HFC-32, or of HFC-32 and HFC-125 such that after about 50 weight percent of an original composition is evaporated or boiled off to produce a remaining composition, the change between the original composition and the remaining composition is typically no more than about 6% and normally no more than about 3% or less relative to the original composition.

It is possible to characterize, in effect, a constant boiling admixture which may appear under many guises, depending upon the conditions chosen, by any of several criteria:

* The composition can be defined as an azeotrope of CFC-115 ("A") and HFC-32 ("B") or of HFC-125 ("C") and HFC-32 ("D"), among others, because the term "azeotrope" is at once both definitive and limitative, and requires effective amounts of A,B (or C,D ) for this unique composition of matter which can be a constant boiling composition.

* It is well known by those skilled in the art, that, at different pressures, the composition of a given azeotrope will vary at least to some degree, and changes in pressure will also change, at least to some degree, the boiling point temperature. Thus, an azeotrope of CFC-115 ("A") and HFC-32 ("B") or of HFC-125 ("C") and HFC-32 ("D"), among others, represents a unique type of relationship but with a variable composition which depends on temperature and/or pressure. Therefore, compositional ranges, rather than fixed compositions, are often used to define azeotropes.

* The composition can be defined as a particular weight percent relationship or mole percent relationship of CFC-115 ("A") and HFC-32 ("B") or of HFC-125 ("C") and HFC-32 ("D"), among others, which recognizing that such specific values point out only one particular relationship and that, in actuality, a series of such relationships, represented by A,B (or C,D) actually exist for a given azeotrope, varied by the influence of pressure.

* An azeotrope of CFC-115 ("A") and HFC-32 ("B") or of HFC-125 ("C") and HFC-32 ("D"), among others, can be characterized by defining the compositions as an azeotrope characterized by a boiling point at a given pressure, thus given identifying characteristics without unduly limiting the scope of the invention by a specific numerical composition, which is limited by and is only as accurate as the analytical equipment available.

The azeotrope or azeotrope-like compositions of the present invention may be formed by operating a conventional distillation apparatus, when practicing the inventive extractive distillation apparatus, and by combining effective amounts of the components by any convenient method including mixing, combining, among others. For best results, a preferred method is to weigh the desired component amounts, and thereafter combine them in an appropriate container.

The aforementioned problems associated with conventional distillation can be overcome in the present invention by adding HFC-32 before distillation. Under the appropriate conditions, HFC-32 forms an azeotrope with the CFC-115 which is not only more volatile than any of the pure components of the mixture being distilled, i.e., HFC-32, CFC-115, or HFC-125; but, also more volatile than any of the other low-boiling azeotropes of the components, e.g., azeotropes of HFC-125/HFC-32 and CFC-115/HFC-125. By adding HFC-32 to a mixture comprising CFC-115 and HFC-125, an azeotropic distillation process can be employed for removing CFC-115 from the other pure components and azeotropes present.

When HFC-125 contains unacceptable concentrations of CFC-115, HFC-32 can be added to form an azeotrope with all the CFC-115 present. Then, the combined HFC-125/CFC-115/HFC-32 mixture may be distilled in a distillation column under conditions sufficient to form an CFC-115/HFC-32 azeotrope. This azeotrope can exit as an overhead stream from the column and HFC-125 can be removed from the column bottom. This process can, for example, reduce an initial 5000 ppm by weight CFC-115 concentration in HFC-125 to below about 100 ppm, most often to less than about 10 ppm.

The aforementioned CFC-115/HFC-32 azeotrope can be formed under a variety of temperatures and pressures. At a temperature of about 0 degrees C. an azeotrope forms consisting essentially of about 72.6 mole % HFC-32 and about 27.4 mole % CFC-115 having a pressure of about 138 psia. Referring now to FIG. 1, FIG. 1 illustrates graphically the results of measurements made at 0 degrees C. showing formation of an azeotropic or azeotrope-like composition consisting essentially of HFC-32 and CFC-115, as indicated by a mixture of about 72.6 mole % HFC-32 and about 27.4 mole % CFC-115 having a higher vapor pressure than either pure component or other CFC-I 15/HFC-32 mixtures at 0° C., with the composition of the vapor space in the maximum pressure region being that of the azeotrope at the specific temperature. Based upon this result and the previously described NRTL references, it was determined that an azeotrope also forms at about 75 degrees C. consisting essentially of about 92.4 mole % HFC-32 and about 7.6 mole % CFC-115 having a pressure of 790 psia; and that an azeotrope also forms at about -50 degrees C consisting essentially of about 70.7 mol % HFC-32 and about 29.3 mole % CFC-115 having a pressure of about 19.4 psia.

The discovery that the CFC-115/HFC-32 azeotropic or azeotrope-like composition varies dependent upon temperature and pressure provides a method if desired of subsequently separating the HFC-32 from the CFC-115, i.e., breaking the azeotrope into its components. If the CFC-115/HFC-32 azeotropic or azeotrope-like composition formed under one temperature/pressure combination is then distilled under a different temperature/pressure combination, the composition of the azeotrope may be changed such that one component, HFC-32 or CFC-115, is now in excess relative to the newly-formed azeotrope composition. The newly formed azeotropic or azeotrope-like composition may then be distilled overhead while the excess component is recovered as column bottoms. HFC-32 in a HFC-32/CFC-115 azeotropic or azeotrope-like composition from the previously described azeotropic distillation may be removed from the CFC-115, if desired, by (1) subsequently distilling the CFC-115/HFC-32 mixture under conditions that form a CFC-115/HFC-32 azeotropic or azeotrope-like composition wherein the CFC-115 concentration in the azeotropic or azeotrope-like composition is less relative to the HFC-32 than in the first mixture, (2) distilling the CFC-15/HFC-32 azeotrope overhead; and (3) recovering the CFC-115 present in excess of the CFC-115/HFC-32 azeotrope as a CFC-115 bottoms product that is substantially-free of HFC-32. By "substantially-free" is meant that the CFC-115 bottoms product contains less than about 500 ppm HFC-32, more typically less than about 50 ppm HFC-32. Conversely, CFC-115 in a HFC-32/CFC-115 azeotropic or azeotrope-like composition from aforementioned azeotropic distillation may be removed from the HFC-32, if desired, by (1) subsequently distilling the CFC-115/HFC-32 mixture under conditions that form a CFC-115/HFC-32 azeotropic or azeotrope-like composition wherein the HFC-32 concentration in the azeotropic or azeotrope-like composition is less relative to the CFC-115 than in the first mixture, (2) distilling the CFC-I 15/HFC-32 azeotrope overhead; and (3) recovering the HFC-32 present in excess of the CFC-115/HFC-32 azeotrope as a HFC-32 bottoms product that is substantially-free of CFC-115. By "substantially-free" is meant that the HFC-32 bottoms product contains less than about 500 ppm CFC-115, more typically less than about 50 ppm CFC-115.

Any residual HFC-32 in the HFC-125 product from the first azeotropic distillation may be removed, if desired, by (1) subsequently distilling the HFC-125/HFC-32 mixture under conditions effective to form an HFC-125/HFC-32 azeotrope, (2) distilling the HFC-125/HFC-32 azeotrope as an overhead product stream; and (3) recovering the HFC-125 present in excess of the HFC-125/HFC-32 azeotrope as a HFC-125 bottoms product, e.g., a HFC-125 product that is substantially-free of HFC-32. By "substantially-free" is meant that the HFC-125 bottoms product contains less than about 500 ppm HFC-32, more typically less than about 50 ppm HFC-32.

Figure 2:
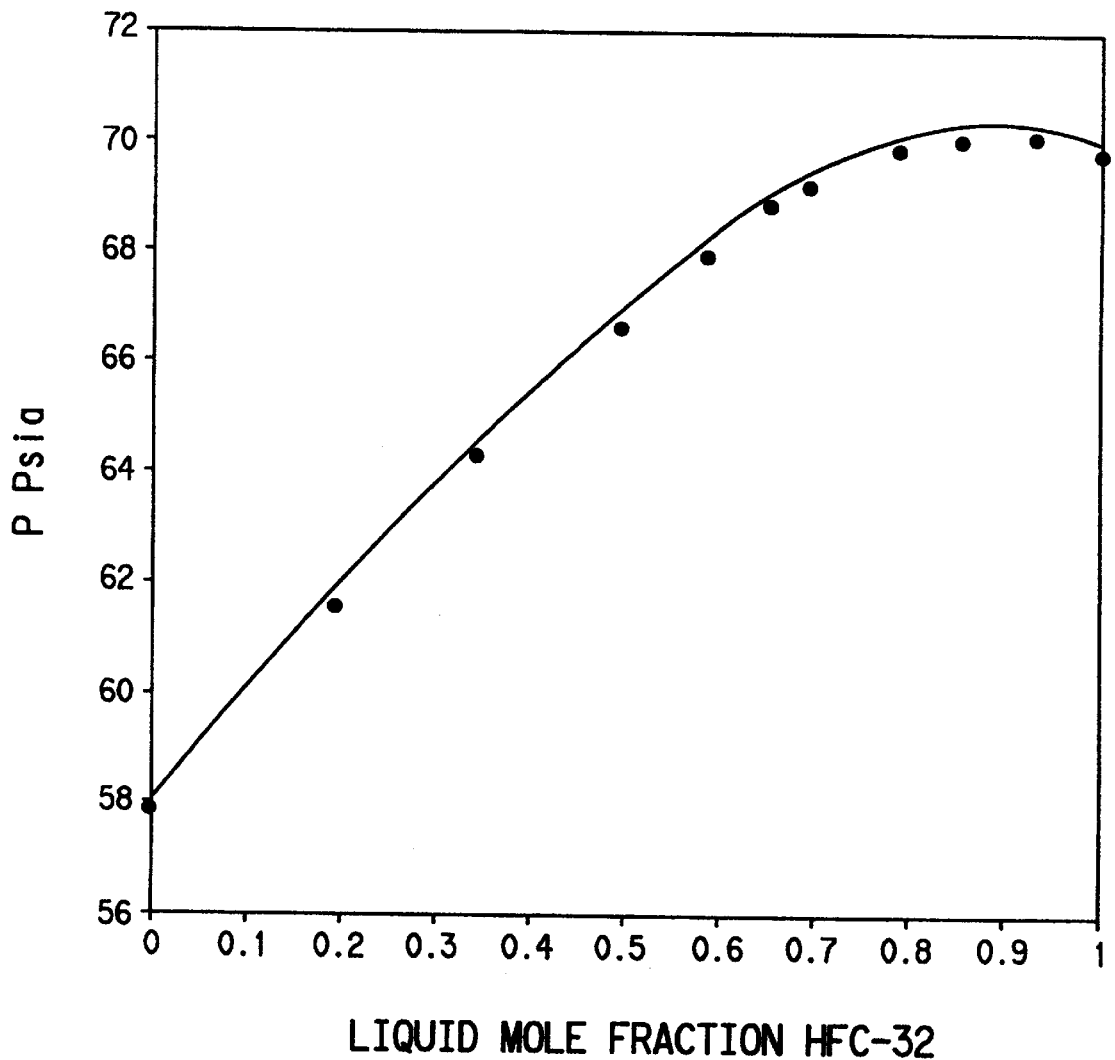
FIG. 2 is a graphical representation at about −15.3° C. of an azeotropic and azeotrope-like composition formed between HFC-32 and HFC-125.

Moreover, the HFC-125/HFC-32 azeotrope can also be formed under a variety of temperatures and pressures. At a temperature of about −15.3 degrees C., an azeotrope can form consisting essentially of about 9.1 mole % HFC-125 and about 90.9 mole % HFC-32 having a pressure of about 70.3 psia. Referring now to FIG. 2, FIG. 2 illustrates graphically the results of measurements made at −15.3 degrees C showing formation of an azeotropic or azeotrope-like composition consisting essentially of HFC-32 and HFC-125, as indicated by mixtures of about 90.9 moles % HFC-32 and about 9.1 mole % HFC-125 having a higher vapor pressure than either pure component or other HFC-32/HFC-125 mixtures at this temperature, with the composition of the vapor space in the maximum pressure region being that of the azeotrope at the specific temperature and pressure. At about 44.0 degrees C., we found an azeotrope forms consisting essentially of about 96.0 mole % HFC-32 and 4.0 mole % HFC-125 having a pressure of about 406 psia. Based upon these results and the previously described NRTL references, we determined that an azeotrope can form at a temperature of about −50 degrees C. consisting essentially of about 84.9 mole % HFC-32 and about 15.1 mole % HFC-125 having a pressure of about 16.2 psia.

The discovery that the HFC-125/HFC-32 azeotrope composition varies dependent upon temperature and pressure also provides a method of separating the components of the HFC-125/HFC-32 azeotrope. For example, if the HFC-125/HFC-32 azeotrope formed under one temperature/pressure combination is then distilled under a different temperature/pressure combination, the composition of the azeotrope may be changed such that one component, HFC-32 or HFC-125, is now in excess relative to the newly formed azeotrope composition. The newly formed azeotrope composition may then be distilled as an overhead product of a distillation column while the excess component can be recovered as column bottoms.

The previously described azeotropic distillation methods are particularly useful when used in conjunction with a method for co-producing HFC-32 and HFC-125. For example, a HFC-125/HFC-32 mixture may be co-produced by contacting mixtures comprising methylene chloride and a chlorotetrafluoroethane (e.g., HCFC-124) with hydrogen fluoride. The HFC-125/HFC-32 product stream may contain unacceptable amounts of CFC-115 which may be removed from the HFC-125/HFC-32 product by distilling the CFC-115/HFC-32 azeotrope as an overhead stream thereby removing the CFC-115 and eliminating any need to separate the HFC-125 and HFC-32. The co-produced HFC-125/HFC-32 product stream may also contain unacceptable amounts of HF which may be removed from the HFC-125/HFC-32 product by distilling the HFC-125/HFC-32 azeotrope as an overhead stream, leaving the HF to exit the column bottoms. As discussed above, when HFC-125 is produced without HFC-32, HFC-32 may be added to allow for the removal of the HF from the HFC-125.

A particularly desirable process permitted by the instant invention relates to HFC-32 that is synthecised with, or subsequently added to an HFC-125 stream which contains HF and CFC-115. The presence of HFC-32 permits the HFC-125 to be separated from the HF in a first column via removal of an HFC-32/HFC-125 azeotrope as distillate, wherein the HF may then be recycled from the bottoms to a fluorination reactor. The presence of HFC-32 also allows for separating CFC-115 from the HFC-125 in a second column by forming the CFC-115/HFC-32 azeotrope and distilling the CFC-115/HFC-32 azeotrope overhead, recovering the HFC-125 from the bottoms as product substantially-free of HF and CFC-115. By "substantially-free" is meant that the HFC-125 product contains less than about 500 ppm of HF and CFC-115, more typically less than about 50 ppm HF and CFC-115.

Figure 3:
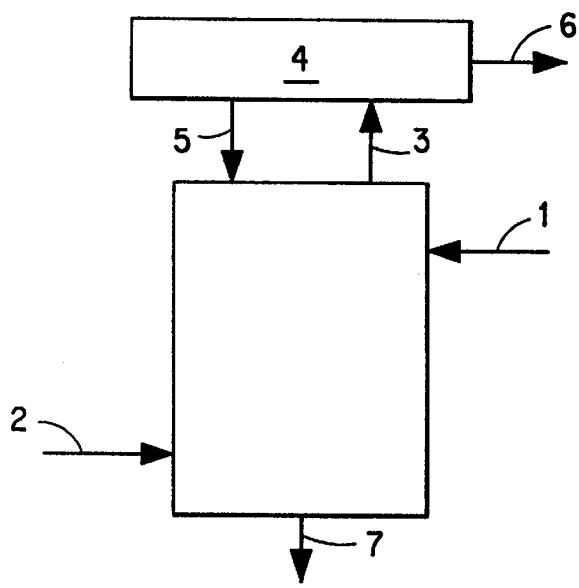
FIG. 3 is a graphical representation of one aspect of the invention for using extractive distillation with HFC-32 to remove HFC-125 from CFC-115 and HCl.

The presence of hydrogen chloride (HCl) in a HFC-125/CFC-115 containing stream further increases the difficulty of separating CFC-115 from HFC-125 compared to instances when HCl is not present. When a CFC-115/HFC-125 mixture also contains HCl, HFC-32 can be employed as an extractant in an extractive distillation that permits efficiently separating HFC-125 from CFC-115 and HCl. Extractive distillation can be employed when the components of a mixture may have differing volatilities; but, such a difference is insufficient to permit effectively separating the components by using conventional distillation. An HFC-32 extractive agent is added that causes the difference in volatilities of the components in the starting mixture to be become amplified such that the relative volatilities become sufficient to permit separation of the components in a distillation column. As previously disclosed in U.S. Pat. No. 5,421,964, which is hereby incorporated by reference, HCl can form a vapor-liquid equilibrium pinch point with HFC-125 and an azeotrope with CFC-115 that makes the separation of HFC-125 or CFC-115 from HCl by conventional distillation both inefficient and expensive. Such interactions further hinder removing CFC-115 from HFC-125 while in the presence of HCl. In accordance with the instant invention, HFC-32 can be employed as an extractant when distilling an HCl/HFC-125/CFC-115 mixture. HCl and CFC-115 are more volatile than HFC-125 when in the presence of HFC-32. Consequently, the HFC-125 can be removed in the bottoms of an extractive distillation column along with HFC-32. This aspect of the invention is shown by FIG. 3. Referring now to FIG. 3, an HFC-32 extraction agent is introduced at an upper feed point 1 of an extractive distillation column; whereas the first mixture requiring separation comprising HCl, CFC-115 and HFC-125, is introduced at a relatively lower point 2 in the column. The HFC-32 extraction agent passes downwardly through trays which are located at the center of the column and contacts a first mixture thereby forming a second mixture. While in the presence of the HFC-32, the HCl and CFC-115 become more volatile than the HFC-125, thereby allowing the HFC-125 to exit the column bottoms relatively free of HCl and CFC-115. The CFC-115 and HCl, which are exiting the top of the column 3 as column off-gas, can be condensed by using conventional reflux condensers 4. At least a portion of this condensed stream can be returned to the column as reflux, and the remainder removed as distillate 6. The HFC-125 and HFC-32 comprise a third mixture that exits from the bottom of the column 7, and can in turn can be recovered as product, or sent to yet another distillation column for separation. The specific conditions which can be used for practicing the invention depend upon a number of parameters such as the diameter of the column, feed points, number of separation stages in the column, among others. The operating pressure of the extractive distillation system may range from about 15 to 350 psia, normally about 50 to 300 psia. Typically, an increase in the HFC-32 feed rate relative to the CFC-115/HFC-125/HCl feed rate causes an increase in the purity of the separated HCl and CFC-115 relative to the HFC-125. Normally, increasing the reflux results in an decreased HFC-32 and HFC-125 in the overhead distillate. The temperature of the condenser, which is located adjacent to the top of the column, is normally sufficient to substantially condense the HCl and CFC-115.

As discussed previously, mixtures of HFC-125 and HFC-32 that are co-produced in accordance with the instant invention or obtained from any other suitable source are difficult to separate due to the formation of an HFC-125/HFC-32 azeotrope. When it is desired that either HFC-125 or HFC-32 be separated from a first mixture of HFC-125 and HFC-32, methylene chloride can also be employed as an extractant in an extractive distillation process that allows for efficient separation of the HFC-125 from the HFC-32. The HFC-32 may subsequently be separated from the methylene chloride by any number of known techniques, including simple distillation. The specific conditions which can be used for practicing the invention also depend upon a number of parameters such as the diameter of the column, feed points, number of separation stages in the column, among others. The operating pressure of the extractive distillation system may range from about 15 to 350 psia, normally about 50 to 300 psia. Typically, an increase in the methylene chloride feed rate relative to the HFC-125/HFC-32 feed rate causes an increase in the purity of the separated HFC-125 relative to the HFC-32. Normally, increasing the reflux results in an decreased methylene chloride in the overhead distillate. The temperature of the condenser, which is located adjacent to the top of the column, is normally sufficient to substantially condense the HFC-125.

While the above description places particular emphasis upon separating certain compounds, the inventive processes can be employed under a wide range of conditions and materials. For example, the processes of the instant invention can be employed to separate CFC-115 from a mixture comprising HFC-143a (1,1,1-trifluoroethane) and CFC-115 by HFC-32, and distilling the HFC-32/CFC-115 azeotrope as an overhead product thereby permitting recovery of HFC-143 a from the column bottom, e.g., HFC-143a that is substantially free of CFC-115. The processes of the instant invention can also be employed for removing HFC-32 from a mixture comprising HFC-143a and HFC-32 by adding CFC-115 and distilling the HFC-32/CFC-115 azeotrope as an overhead product thereby permitting recovery of HFC-143a from the column bottom, e.g., HFC-143a that is substantially free of HFC-32. Alternatively, HFC-32 can be removed from a mixture comprising HFC-143a/HFC-32/CFC-115 by distilling the HFC-32/CFC-115 azeotrope overhead. Further, the instant invention can be employed for removing CFC-115 from a mixture comprising HCFC-22 (chlorodifluoromethane) and CFC-115 by adding HFC-32 and distilling the HFC-32/CFC-115 azeotrope as an overhead product thereby recovery of HCFC-22 from the column bottom, e.g, HCFC-22 that is substantially free of CFC-115. Alternatively, CFC-115 can be removed from a mixture comprising HCFC-22/CFC-115/HFC-32 by distilling the HFC-32/CFC-115 azeotrope as an overhead product. Further still, the instant invention can be employed for removing CFC-115 from a wide range of fluorocarbon containing blends or mixtures containing one or more members from the group of HCFC-22, HFC-32, HFC-125, HFC-134, HFC-134a, HFC-143a, among others.

Certain aspects of the invention are demonstrated by the following Examples. These examples are provided only to further illustrate certain aspects of the inventive processes and not limit the scope of the appended claims. In the following Examples and Comparative Examples, "ppm" and "ppmw" are the parts-per-million-by-weight concentration of a compound in the identified stream. In the following Examples and Comparative Examples, "pph" and "lbs./hr" are the pounds-per-hour flowrate of the designated compound or stream.

Comparative Example 1

In this Comparative Example, a steam containing 1000 pph HFC-125 and 5 pph CFC-115 is fed to a distillation column containing 101 stages assumed to operate at 100% efficiency. The goal was to obtain HFC-125 containing 10 ppm by weight CFC-115. The column is operating at 194.7 psia, the condenser is operating at 23.8 deg C. and the reboiler at 24.4 deg C. The feed is entering at −25 deg C. The reflux rate was varied to see the effect on HFC-125 composition. The results are shown in Table 4.

TABLE 4

| Reflux Flow | Distillate | | Tails | | % 125 |
|---|---|---|---|---|---|
| | PPH 125 | Wt. % 115 | PPH 125 | PPM 115 | Recovery |
| 100000 | 499 | 1.06 | 501 | 2116 | 50 |
| 200000 | 499 | 0.97 | 501 | 1936 | 50 |
| 300000 | 499 | 0.94 | 501 | 1871 | 50 |

In this example, separation is attempted by conventional distillation, with the HFC-125 product taken overhead, the CFC-115 leaving in the tails stream. The tails rate was set at approximately 50% of the incoming feed rate. Even with a substantial amount of HFC-125 being removed in the tails stream and an extremely high reflux flow, the HFC-125 product does not even begin to approach the desired purity. The efficiency with which CFC-115 may be separated from HFC-125 by conventional distillation is limited.

EXAMPLE 1

In this Example, azeotropic distillation is used to separate CFC-115 from a mixture with HFC-125 by adding HFC-32 to the mixture. Approximately 1.5 lbs./hr HFC-32 is added to a first stream of 99.5 lbs./hr HFC-125 and 0.5 lbs./hr CFC-115. The combined stream is then fed to a distillation column. The distillation column has 72 stages assumed to operate at 100% efficiency basis (with the column condenser being designated as stage 1). The feed mixture is fed in on stage 15 at −15 degrees C. The column operates under conditions such that the azeotrope of CFC-115 and HFC-32 forms and is distilled overhead, wherein this overhead off-gas is condensed and some fraction returned to the column as reflux; the remainder is removed as the column distillate.

The column operates at about 80 psig, with the condenser operating at −9 degrees C. and the reboiler operating at 0 degrees C. The column bottoms is removed from the column as HFC-125 product.

The following table (Table 5) shows the various column flow rates and compositions, with the product of this Example obtained from the Column Bottoms flow.

TABLE 5

Column Flows in Lbs. per Hour

| Component | Column Feed | Column Off-Gas | Column Reflux | Column Distillate | Column Bottoms |
|---|---|---|---|---|---|
| HFC-32 | 1.500 | 442.190 | 440.789 | 1.401 | 0.099 |
| CFC-115 | 0.500 | 157.516 | 157.016 | 0.499 | 0.001 |
| HFC-125 | 99.500 | 145.839 | 145.377 | 0.462 | 99.038 |

This Example shows that adding HFC-32 to a first mixture comprising HFC-125 and CFC-115, then distilling the combined mixture under conditions such that the CFC-115/HFC-125 azeotrope forms and is distilled overhead, permits removing substantially all of the CFC-115 from the first mixture, i.e., produces a HFC-125 that is substantially free of CFC-115. Calculations indicate the Column Bottoms HFC-125 contains about 10 ppm by weight CFC-115. In this case the undesirable CFC (115) is replaced with a lower level of more-acceptable HFC (32). The 32 consumption for this case is approximately 3 lbs. HFC-32 per lb. of CFC-115 removed. Such an amount of HFC-32 is in excess of the HFC-32/CFC-115 azeotrope composition, and so the amount of HFC-32 used in this Example could be reduced if desired.

EXAMPLE 2

Figure 4:
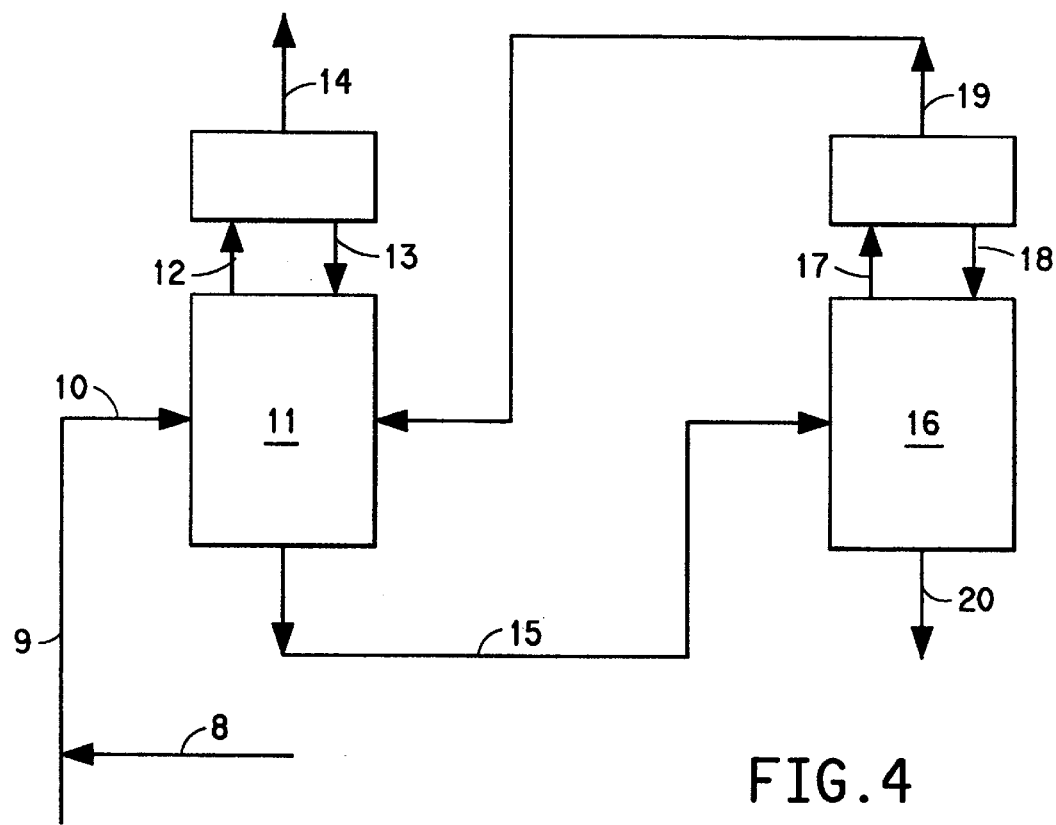
FIG. 4 is a graphical representation of another aspect of the invention for using azeotropic distillation with HFC-32 to remove CFC-115 from HFC-125.

In this Example a second azeotropic distillation is used in combination with the first distillation described in Example 1 to separate and reduce the quantity of residual HFC-32 in the HFC-125 product. In this second distillation, the residual HFC-32 is removed overhead as the HFC-125/HFC-32 azeotrope. The stream numbers referred to in this Example correspond to those shown in FIG. 4. Referring now to FIG. 4, approximately 1.5 lbs./hr HFC-32 8 is added to a first stream of 99.5 lbs./hr HFC-125 and 0.5 lbs./hr CFC-115 9. The combined stream 10 is then fed to a first distillation column 11, with its design and operating conditions as described in Example 1.

The first column operates under conditions such that an azeotrope of CFC-115 and HFC-32 forms and is distilled overhead 12, wherein this overhead off-gas is condensed and some fraction returned to the column as reflux 13, with the remainder removed as the column distillate 14. The column bottoms stream 15 is fed to a second distillation column 16.

This second column 16 has 57 stages assumed to operate at 100% efficiency (with the column condenser designated as stage 1). The feed mixture is fed in onto stage 25 at a temperature of about 0 degrees C. The column operates at about 95 psia, with the condenser operating at about −1 degrees C. and the reboiler operating at about 0 degrees C. This second column is operated so that an HFC-125/HFC-32 azeotrope forms and is distilled overhead 17, wherein this overhead off-gas is condensed and some fraction returned to the column as reflux 18. The remainder is removed as the column distillate 19 which is returned to the first column 11 on stage 15. The second column's bottoms stream 20 is the final HFC-125 product.

The following table (Table 6) shows the various column flow rates and compositions, with the product of this Example obtained from the second column's Column Bottoms flow.

TABLE 6

First Column Flows in Lbs. per Hour

| Stream # | Makeup HFC-32 8 | Crude HFC-125 9 | Column New Feed 10 | Recycle Feed 19 | Column Off-Gas 12 | Column Reflux 13 | Column Distill. 14 | Column Bottom 15 |
|---|---|---|---|---|---|---|---|---|
| Component | | | | | | | | |
| HFC-32 | 1.500 | 0.000 | 1.500 | 0.107 | 487.826 | 486.328 | 1.498 | 0.109 |
| CFC-115 | 0.000 | 0.500 | 0.500 | <0.001 | 162.548 | 162.048 | 0.500 | <0.001 |
| HFC-125 | 0.000 | 99.500 | 99.500 | 9.893 | 164.290 | 163.786 | 0.504 | 108.889 |

Second Column Flows in Lbs. per Hour

| Stream # | Column Feed 15 | Column Off-Gas 17 | Column Reflux 18 | Column Distillate 19 | Column Bottoms 20 |
|---|---|---|---|---|---|
| HFC-32 | 0.109 | 4.279 | 4.172 | 0.107 | 0.002 |
| CFC-115 | <0.001 | 0.005 | 0.005 | <0.001 | <0.001 |
| HFC-125 | 108.889 | 505.715 | 495.822 | 9.893 | 98.996 |

This Example shows that adding HFC-32 to a first mixture comprising HFC-125 and CFC-115, then distilling the combined mixture under conditions such that an CFC-115/HFC-32 azeotrope is formed and is distilled overhead, permits removing substantially all of the CFC-115 from the product HFC-125. The first column's Column Bottoms HFC-125 contains about 10 ppm by weight CFC-115, the undesirable CFC-115 being replaced with a lower level of more-acceptable HFC-32. In those instances when this residual HFC-32 in the HFC-125 is not desirable, this example shows how HFC-32 may then be reduced by distilling it in a column operated so that the HFC-125/HFC-32 azeotrope is formed and distilled overhead, removing HFC-32 from the bottoms product HFC-125.

EXAMPLE 3

In this Example, approximately 49.75 lbs./hr HFC-32 is added to a first stream comprising approximately 49.75 lbs./hr HFC-125 and 0.50 lbs./hr CFC-115 from which we want to remove CFC-115. The combined stream is then fed to a distillation column. The column has 32 stages assumed to operate at 100% efficiency (with the column condenser designated as stage 1). The feed mixture is fed in onto stage 10 at a temperature of about −15 degrees C. The column operates at about 80 psig, with the condenser operating at about −11 degrees C. and the reboiler operating at about −5 degrees C.

The following table (Table 7) shows the various column flow rates and compositions, with the product of this Example shown in the Column Bottoms flow.

TABLE 7

Column Flows in Lbs. per Hour

| Component | Column Feed | Column Off-Gas | Column Reflux | Column Distillate | Column Bottoms |
|---|---|---|---|---|---|
| HFC-32 | 49.750 | 235.360 | 234.891 | 0.469 | 49.281 |
| CFC-115 | 0.500 | 250.427 | 249.927 | 0.500 | <0.001 |
| HFC-125 | 49.750 | 15.212 | 15.182 | 0.030 | 49.720 |

This Example shows that adding HFC-32 to a first mixture comprising HFC-125 and CFC-115, then distilling the combined mixture under conditions such that the CFC-115/HFC-32 azeotrope forms and is distilled overhead permits removing substantially all of the CFC-115 from the HFC-125/HFC-32 product stream, thus producing HFC-125/HFC-32 as a bottoms product substantially free of CFC-115, i.e., containing about 5 ppm by weight CFC-115.

EXAMPLE 4

Example 4 is analogous to Example 3, except that the column contains 57 stages assumed to operate at 100% efficiency, and uses a lower reflux rate. The column feed enters onto stage 12, the condenser is operating at a temperature of about −10 degrees C., the reboiler is operating at about −5 degrees C., and the column is operating at about 80 psig.

The following table (Table 8) shows the various column flow rates and compositions, with the product of this Example shown in the Column Bottoms flow.

TABLE 8

Column Flows in Lbs. per Hour

| Component | Column Feed | Column Off-Gas | Column Reflux | Column Distillate | Column Bottoms |
|---|---|---|---|---|---|
| HFC-32 | 49.750 | 105.579 | 104.867 | 0.712 | 49.038 |
| CFC-115 | 0.500 | 73.979 | 73.479 | 0.500 | <0.001 |
| HFC-125 | 49.750 | 21.801 | 21.654 | 0.147 | 49.603 |

This Example shows that results equivalent to Example 3 can be obtained at a much lower reflux ratio by adding additional stages to the column.

Comparative Example 2

In this Comparative Example, 2080 lbs./hr HFC-125 and 3810 lbs./hr HF are fed to a distillation column. The distillation column has 62 stages assumed to operate at a 100% efficiency (with the column condenser being designated as stage 1). The feed mixture is fed in on stage 45 at −10 degrees C.

The column operates at about 100 psig, with the condenser operating at 4.6 degrees C. and the reboiler operating at 63.1 degrees C. The reflux ratio is 2/1, and the distillate/feed ratio is 0.995 (based on HFC-125 feed flow only).

The following table (Table 9) shows the results of this distillation.

TABLE 9

Column Flows in Lbs. per Hour

| Component | Column Feed | Column Reflux | Column Distillate | Column Bottoms |
|---|---|---|---|---|
| HFC-125 | 2080 | 3487 | 1744 | 336 |
| HF | 3810 | 108 | 54 | 3756 |

In this example, the higher boiling HF exits the column bottoms, while the HFC-125 exits overhead. However, there remains substantial HF in the HFC-125 overhead due to the azeotrope that forms between HF and HFC-125. This consequently limits the removal efficiency of HF from a product HFC-125 by conventional distillation.

Comparative Example 3

This Comparative Example is analogous to Comparative Example 2, except that the reflux ratio has been increased to 100/1. The following table (Table 10) shows the results of this distillation.

TABLE 10

Column Flows in Lbs. per Hour

| Component | Column Feed | Column Reflux | Column Distillate | Column Bottoms |
|---|---|---|---|---|
| HFC-125 | 2080 | 174380 | 1744 | 336 |
| HF | 3810 | 5431 | 54 | 3756 |

This Comparative Example shows that in spite of significantly increasing the reflux ratio, the efficiency of the separation of HF from the HFC-125 exiting overhead has not increased, due to the existence of a HF/HFC-125 azeotrope.

Comparative Example 4

In this Comparative Example, 2080 lbs./hr HFC-32 and 3810 lbs./hr HF are fed to a distillation column. The distillation column has 42 stages assumed to operate at 100% efficiency (with the column condenser being designated as stage 1). The feed mixture is fed in on stage 25 at −10 degrees C.

The column operates at about 100 psig, with the condenser operating at −0.86 degrees C. and the reboiler operating at 89.1 degrees C. The reflux ratio is 1/1, and the distillate/feed ratio is 0.998 (based on HFC-32 feed flow only).

The following table (Table 11) shows the results of this distillation.

TABLE 11

Column Flows in Lbs. per Hour

| Component | Column Feed | Column Reflux | Column Distillate | Column Bottoms |
|---|---|---|---|---|
| HFC-32 | 2080 | 2076 | 2076 | 4 |
| HF | 3810 | 0.001 | 0.001 | 3810 |

In this example, the higher-boiling HF exits the column bottoms, while the HFC-32 exits overhead. This Comparative Example can be compared to Comparative Example 3 where a larger column and a much higher reflux ratio is used to remove HF from HFC-125. This Comparative Example shows it is much easier to separate HF from HFC-32 than it is to remove HF from HFC-125 by conventional distillation. This is because HFC-32 does not form an azeotropic or azeotrope-like composition with HF.

EXAMPLE 5

This Example is identical to Comparative Example 2, except that HFC-32 has been added to the column feedstream, the condenser is operating at 0 degrees C., the reboiler is operating at 88 degrees C. and the distillate/feed ratio is 0.995 based on the feed flows of HFC-32 plus HFC-125. The following table (Table 12) shows the results of this distillation.

TABLE 12

Column Flows in Lbs. per Hour

| Component | Column Feed | Column Reflux | Column Distillate | Column Bottoms |
|---|---|---|---|---|
| HFC-125 | 2080 | 4159 | 2080 | 0.018 |
| HF | 3810 | <0.001 | <0.001 | 3810 |
| HFC-32 | 2080 | 4130 | 2065 | 15 |

This example shows a significant reduction in the HF exiting with the HFC-125 even while operating at a relatively low reflux ratio. It also shows a significant increase in the amount of the HFC-125 fed that is recovered as a deacidified overhead product. This Example shows the value of adding or having HFC-32 in combination with HFC-125 for the separation of HF and HFC-125.

Comparative Example 5

In this Example, an off-gas stream from a reaction that produces HFC-125 as a product is fed to a distillation column. The column has 62 stages assumed to operate at 100% efficiency (with the column condenser designated as stage 1). The feed mixture is fed in onto stage 45 at a temperature of about −10 degrees C. The column operates at about 100 psig, with the condenser operating at about 4.58 degrees C. and the reboiler operating at about 47.30 degrees C. The reflux ratio is 20/1. The following table (Table 13) shows the various column flow rates and compositions resulting from this example.

TABLE 13

Column Flows in Lbs. per Hour

| Component | Column Feed | Column Reflux | Column Distillate | Column Bottoms |
|---|---|---|---|---|
| HF | 3810.00 | 1091.35 | 54.57 | 3755.43 |
| F114a | 600.00 | <0.0001 | <0.0001 | 600.00 |
| F115 | 18.00 | 353.16 | 17.66 | 0.34 |
| F123 | 3050.00 | <0.0001 | <0.0001 | 3050.00 |
| F124 | 8420.00 | <0.0001 | <0.0001 | 8420.00 |
| F125 | 2080.00 | 34854.00 | 1742.44 | 337.56 |
| F133a | 375.00 | <0.0001 | <0.0001 | 375.00 |
| F134a | 15.00 | <0.0001 | <0.0001 | 15.00 |

Where:
HF = Hydrogen Fluoride
F114a = dichlorotetrafluoroethane (CFC-114a)
F115 = chloropentafluoroethane (CFC-115)
F123 = dichlorotrifluoroethane (HCFC-123)
F124 = chlorotetrafluoroethane (HCFC-124)
F125 = pentafluoroethane (HFC-125)
F133a = chlorotirfluoroethane (HCFC-133a)
F134a = tetrafluoroethane (HFC-134a)

This Comparative Example shows that, similar to Comparative Example 2, in the conventional distillation of the off-gas from a HFC-125 synthesis, HF cannot be efficiently removed from the HFC-125 exiting overhead due to the formation of the HFC-125/HF azeotrope.

EXAMPLE 6

This Example is identical to Comparative Example 5 except that HFC-32 has now been added to the columns feed stream.

The following table (Table 14) shows the various column flow rates and compositions resulting from this example.

TABLE 14

Column Flows in Lbs. per Hour

| Component | Column Feed | Column Reflux | Column Distillate | Column Bottoms |
|---|---|---|---|---|
| HF | 3810.00 | 1.43 | 0.07 | 3809.93 |
| F32 | 2080.00 | 41539.00 | 2076.94 | 3.06 |
| F114a | 600.00 | <0.0001 | <0.0001 | 600.00 |
| F115 | 18.00 | 359.97 | 18.00 | 0.0013 |
| F123 | 3050.00 | <0.0001 | <0.0001 | 3050.00 |
| F124 | 8420.00 | <0.0001 | <0.0001 | 8420.00 |
| F125 | 2080.00 | 41043.00 | 2052.17 | 27.83 |
| F133a | 375.00 | <0.0001 | <0.0001 | 375.00 |
| F134a | 15.00 | <0.0001 | <0.0001 | 15.00 |

Where:
HF = Hydrogen Fluoride
F32 = difluoromethane (HFC-32)
F114a = dichlorotetrafluoroethane (CFC-114a)
F115 = chloropentafluoroethane (CFC-115)
F123 = dichlorotrifluoroethane (HCFC-123)
F124 = chlorotetrafluoroethane (HCFC-124)
F125 = pentafluoroethane (HFC-125)
F133a = chlorotirfluoroethane (HCFC-133a)
F134a = tetrafluoroethane (HFC-134a)

This Example shows that adding HFC-32 to a first mixture comprising HFC-125 and CFC-115, then distilling the combined mixture under conditions such that the HFC-32/HFC-125 azeotrope or azeotrope-like composition is formed and distilled overhead permits removing substantially all of the HF from the HFC-125/HFC-32 product stream, thus producing HFC-125/HFC-32 as a overhead product substantially free of HF, e.g., containing about <5 ppm by weight HF. To subsequently remove the CFC-115 from the HFC-32/HFC-125 product stream, and/or the HFC-32 from the HFC-125, the inventive azeotropic distillation shown in the prior examples can be employed.

Comparative Example 6

In this Comparative Example, a stream consisting of 2100 pph HFC-125, 15 pph CFC-115 and 600 pph HCl is fed to a distillation column, equivalent to HFC-125 containing 7092 ppm by weight CFC-115 on an organics-only basis. The distillation column has 72 stages assumed to operate at 100% efficiency, and is operated at 250 psig. The Condenser is operating at −13 degrees C., the bottoms at 36 degrees C. The reflux flow is 10,000 pph. The feed stream is fed to the column entering at stage 40 (with the condenser designated as stage 1). The goal of this distillation is to produce HFC-125 containing 100 ppm or less of CFC-115.

The results of this distillation are shown in Table 15.

TABLE 15

| | Column Flows in PPH | | |
|---|---|---|---|
| | Column Feed | Column Distillate | Column Bottoms |
| HFC-125 | 2100.00 | 18.50 | 2081.50 |
| CFC-115 | 15.00 | 1.65 | 13.35 |
| HCl | 600.00 | 600.00 | <0.01 |

As may be seen, the results show this is completely ineffective in providing the desired results. The HFC-125 exiting the column as bottoms has 6373 ppmw CFC-115 [expressed as the ratio of CFC-115/(CFC-115 +HFC-125)]. This negligible change in CFC-115 content of the product versus the feed is also accompanied by almost 0.9% of HFC-125 fed in with the feed stream leaving with the overhead distillate.

Comparative Example 7

This Comparative Example is identical to Comparative Example 8, except that in this Comparative Example, the HCl feed is fed in at stage 40, while the HFC-125 and CFC-115 are fed in at stage 15.

The results of this distillation are shown in Table 16.

TABLE 16

| | Column Flows in PPH. | | |
|---|---|---|---|
| | Column Feed | Column Distillate | Column Bottoms |
| HFC-125 | 2100.00 | 33.20 | 2066.80 |
| CFC-115 | 15.00 | 1.87 | 13.13 |
| HCL | 600.00 | 595.50 | 4.50 |

Even with shifting the feed point of the HFC-125/CFC-115 relative to the HCl which would be expected to enhance the HCl function as an entraining agent, this remains completely ineffective in providing the desired results. The HFC-125 exiting the column as bottoms has 6312 ppmw CFC-115 [expressed as the ratio of CFC-115/(CFC-115+ HFC-125)]. The negligible change in CFC-115 content is also accompanied by almost 1.6% of HFC-125 fed in with the feed stream leaving with the overhead distillate, a reduction in HFC-125 recovery versus Comparative Example 6.

Comparative Example 8

This Comparative Example is identical to Comparative Example 7, except that in this Comparative Example the reflux flow has been increased to 40,000 pph, the column pressure reduced to 150 psig, the distillate temperature is −28 degrees C. and the bottoms temperature is 18 degrees C.

The results of this distillation are shown in Table 17.

TABLE 17

| | Column Flows in PPH | | |
|---|---|---|---|
| | Column Feed | Column Distillate | Column Bottoms |
| HFC-125 | 2100.00 | 27.50 | 2072.50 |
| CFC-115 | 15.00 | 6.52 | 8.48 |
| HCl | 600.00 | 596.10 | 3.90 |

Increasing the distillate rate is still not effective in achieving the desired result. The HFC-125 exiting the column as bottoms has 4075 ppmw CFC-115 [expressed as the ratio of CFC-115/(CFC-115+HFC-125)]. This negligible change in CFC-115 content is also accompanied by almost 1.3% of the HFC-125 fed in with the feed stream leaving with the overhead distillate.

Comparative Example 9

This Comparative Example is identical to Comparative Example 8, except that in this Comparative Example the HCl feed rate is increased to 5000 pph.

The results of this distillation are shown in Table 18.

TABLE 18

| | Column Flows in PPH | | |
|---|---|---|---|
| | Column Feed | Column Distillate | Column Bottoms |
| HFC-125 | 2100.00 | 285.00 | 1815.00 |
| CFC-115 | 15.00 | 13.77 | 1.23 |
| HCl | 5000.00 | 4960.30 | 39.70 |

Increasing the HCl feed rate is still not effective in achieving the desired result. The HFC-125 exiting the column as bottoms has 677 ppmw CFC-115 [expressed as the ratio of CFC-115/(CFC-115+HFC-125)]. This insufficient change in CFC-115 content is also accompanied by almost 13.5% of the HFC-125 fed in with the feed stream leaving with the overhead distillate, a significant recovery loss of HFC-125. The above Comparative Examples 6,7,8, and 9 show that distilling HFC-125, CFC-115 and HCl using conventional distillation is ineffective in obtaining low CFC-115 content HFC-125 simultaneously with high HFC-125 recovery.

Comparative Example 10

This Comparative Example is identical to Comparative Example 6, except that in addition HFC-32 is fed at 2100 pph, and is fed in at the same stage as the other components (stage 40).

The results of this distillation are shown in Table 19.

TABLE 19

| | Column Flows in PPH | | |
|---|---|---|---|
| | Column Feed | Column Distillate | Column Bottoms |
| HFC-125 | 2100.00 | 17.80 | 2082.20 |
| CFC-115 | 15.00 | 2.89 | 12.11 |
| HCl | 600.00 | 599.93 | 0.07 |
| HFC-32 | 2100.00 | <0.01 | 2100.00 |

Adding HFC-32 as a feed component that is introduced at the same distillation column stage as the other components is still not effective in achieving the desired result. The HFC-125 exiting the column as bottoms contains 5782 ppmw CFC-115 [expressed as the ratio of CFC-I 15/(CFC-115+HFC-125)].

EXAMPLE 7

This Example is identical to Comparative Example 10, except that the HFC-32 is fed in at stage 20, while the HCl, HFC-125, CFC-115 feed stream are fed in at stage 50. I.E., the HFC-32 is used as an extraction agent in this distillation. The results of this distillation are shown in Table 20.

TABLE 20

| | Column Flows in PPH | | |
|---|---|---|---|
| | Column Feed | Column Distillate | Column Bottoms |
| HFC-125 | 2100.00 | 2.84 | 2097.16 |
| CFC-115 | 15.00 | 14.84 | 0.16 |
| HCl | 600.00 | 600.00 | <0.01 |
| HFC-32 | 2100.00 | 2.33 | 2097.67 |

This Example shows several distinct differences from and advantages compared to the previous Comparative Examples 6,7,8,9, and 10. In contrast to the previous examples, the HFC-125 product obtained by operating in accordance with this Example contains only 76 ppmw CFC-115 [expressed as the ratio of CFC-115/(CFC-115+ HFC-125)], i.e. it is effective in obtaining the desired low CFC-115 content in the HFC-125. It does so with a high HFC-125 recovery, i.e. 99.9% of the HFC-125 fed is actually recovered as product. It does so with virtually no HCl exiting the column with the main HFC-125 stream, i.e., effective separation of the HCl and HFC-125. This is a surprising and unexpected result when considering the difficulties demonstrated in effecting the HCl, CFC-115 and HFC-125 separations in the previous Comparative Examples. This Example demonstrates that in order for effective separation, the HFC-32 must be fed into the column above the main feed containing the HCl, CFC-115 and HFC-125, i.e., the HFC-32 is used as an extracting agent in an extractive distillation for the efficient separation of HFC-125 from HCl and CFC-115 from an HFC-125/HCl/ CFC-115 containing mixture rather than simply being co-fed into the column in the same stream as the HCl, HFC-125 and CFC-115.

EXAMPLE 8

This Example is identical to Example 7, except that the HFC-32 is fed at 1050 pph onto stage 15, while the HCl, CFC-115, HFC-125 mixture is fed in at the same flow rates as in Example 7 but onto stage 40.

The results of this distillation are shown in Table 21.

TABLE 21

| | Column Flows in PPH | | |
|---|---|---|---|
| | Column Feed | Column Distillate | Column Bottoms |
| HFC-125 | 2100.00 | 8.17 | 2091.83 |
| CFC-115 | 15.00 | 14.90 | 0.10 |
| HCl | 600.00 | 600.00 | <0.01 |
| HFC-32 | 1050.00 | <0.01 | 1050.00 |

In contrast to Comparative Examples 6,7,8,9, and 10, the HFC-125 product contains 48 ppm CFC-115 [expressed as the ratio of CFC-115/(CFC-115+HFC-125)], i.e. it is effective in obtaining the desired low CFC-115 content in the HFC-125. It does so with high HFC-125 recovery, i.e. 99.6% ofthe HFC-125 fed is actually recovered as product. It does so with virtually no HCl exiting the column with the main HFC-125 stream, i.e., effective separation of the HCl and HFC-125.

EXAMPLE 9

This Example is identical to Example 8, except that the HFC-32 is fed at 525 pph.

The results of this distillation are shown in Table 22.

TABLE 22

| | Column Flows in PPH | | |
|---|---|---|---|
| | Column Feed | Column Distillate | Column Bottoms |
| HFC-125 | 2100.00 | 9.01 | 2090.99 |
| CFC-115 | 15.00 | 13.83 | 1.17 |
| HCl | 600.00 | 600.00 | <0.01 |
| HFC-32 | 525.00 | <0.01 | 525.00 |

The HFC-125 product contains 559 ppm CFC-115 [expressed as the ratio of CFC-115/(CFC-115+HFC-125)], i.e. it is no longer as effective in obtaining the desired low CFC-115 content in the HFC-125. This Example shows that the ppm CFC-115 in the HFC-125 is controllable by adjusting the HFC-32 extractant feed rate, with higher removal at higher HFC-32 feed rates.

EXAMPLE 10

In this Example, a feed stream comprising the reaction off-gas product from a HFC-125 process is fed to a first distillation column containing 82 stages assumed to operate at 100% efficiency, with the condenser designated as stage 1. This reactor off-gas is fed to the column onto stage 50 at a temperature of 34 degrees C. The column is operated at 250 psig pressure, with the condenser operating at −13 deg C., the reboiler operating at 50 degrees C. and with a reflux ratio of about 1.7. A second feed stream comprising HFC-32 and HCl produced as part of the reaction off-gas product from a HFC-32 process is fed to the same distillation column onto stage 20 at a temperature of −11 degrees C.

The bottoms of the first column is then sent on as feed to a second column. The second column contains 62 stages assumed to operate at 100% efficiency, with the condenser designated as stage 1 and the feed to this column fed onto stage 45. The column is operated at 100 psig, the condenser operates at 0 degrees C., the reboiler operates at 53 degrees C. and the column operates with a reflux ratio of about 1.

The results of this distillation are shown in Table 23.

TABLE 23

| | First Column Flows in Pounds Per Hour | | | |
|---|---|---|---|---|
| | Column Feeds | | Column | Column |
| | Stage 50 | Stage 20 | Distillate | Bottoms |
| HF | 3808.66 | 0.02 | <0.01 | 3808.68 |
| HCl | 614.98 | 2902.00 | 3515.98 | <0.01 |
| F32 | 0.0 | 2070.00 | 2.72 | 2070.00 |
| F114a | 117.71 | 0.00 | <0.01 | 117.71 |
| F115 | 13.34 | 0.00 | 13.30 | 0.03 |
| F123 | 528.12 | 0.00 | <0.01 | 528.12 |
| F124 | 1743.82 | 0.00 | <0.01 | 1743.82 |
| F125 | 2072.53 | 0.00 | 6.53 | 2066.00 |

TABLE 23-continued

| | | | | |
|---|---|---|---|---|
| F133a | 66.82 | 0.00 | <0.01 | 66.82 |
| F134a | 6.39 | 0.00 | <0.01 | 6.39 |

Second Column Flows in Pounds Per Hour

| | Column Feed | Column Distillate | Column Bottoms |
|---|---|---|---|
| HF | 3808.68 | 0.52 | 3808.16 |
| HCl | <0.01 | <0.01 | <0.01 |
| F32 | 2083.84 | 2067.28 | 16.56 |
| F114a | 117.71 | 0.42 | 117.29 |
| F115 | 0.03 | 0.03 | <0.01 |
| F123 | 528.12 | <0.01 | 528.12 |
| F124 | 1743.82 | <0.01 | 1743.82 |
| F125 | 2066.00 | 2065.87 | 0.13 |
| F133a | 66.82 | <0.01 | 66.82 |
| F134a | 6.39 | 0.48 | 5.91 |

Where:
HF = Hydrogen Fluoride
HCl = Hydrogen Chloride
F32 = difluoromethane (HFC-32)
F114a = dichlorotetrafluoroethane (CFC-114a)
F115 = chloropentafluoroethane (CFC-115)
F123 = dichlorotrifluoroethane (HCFC-123)
F124 = chlorotetrafluoroethane (HCFC-124)
F125 = pentafluoroethane (HFC-125)
F133a = chlorotrifluoroethane (HCFC-133a)
F134a = tetrafluoroethane (HFC-134a)

This example shows how the aspects of the invention may be effectively combined to obtain significantly increased separation of several of the original feed stream components, and most particularly a HFC-125 product stream substantially free of CFC-115, HF, and HCl.

Comparative Example 11

In this Comparative Example, a fresh feed stream consisting of HFC-32 and HFC-125 is fed to a first distillation column operated to separate the HFC-32 from the HFC-125. The column has 92 stages assumed to operate at 100% efficiency, with the condenser designated as stage 1. The column is 60 inches in diameter. The fresh feed stream contains equal weights of HFC-32 and HFC-125 and is fed onto stage 40 at −10 degrees C. The distillate from a second column that is fed back to this first column as a recycle feed stream also contains HFC-32 and HFC-125, and is also fed onto stage 40 of the first column. The condenser is operating at 24.1 degrees C., the reboiler is operating at 32.5 degrees C., and the column is operating at 225 psig pressure.

The distillate from the first column is then fed as the feed to a second column. This second column has 92 stages assumed to operate at 100% efficiency, with the condenser designated at stage 1. This second column is 87 inches in diameter. The feed stream is fed onto stage 40. The condenser is operating at −46.0 degrees C., the reboiler is operating at −43.7 degrees C., and the column is operating at 5 psig.

The results of these distillations are shown in Table 24.

TABLE 24

First Column Flows in Lbs Per Hour

| | Column Fresh Feed | Recycle Feed | Column Reflux | Column Distillate | Column Bottoms |
|---|---|---|---|---|---|
| HFC-125 | 2070.00 | 1614.53 | 18615.00 | 1616.61 | 2067.92 |
| HFC-32 | 2070.00 | 3140.18 | 71380.00 | 6199.28 | 0.90 |

TABLE 24-continued

Second Column Flows in Lbs. Per Hour

| | Column Feed | Column Reflux | Column Distillate | Column Bottoms |
|---|---|---|---|---|
| HFC-125 | 1616.61 | 25296.00 | 1614.53 | 2.08 |
| HFC-32 | 6199.28 | 64704.00 | 4130.18 | 2069.10 |

This Comparative Example shows that even with extremely large columns with many stages and an extremely high rate of reflux, a high efficiency of separation of the HFC-32 and HFC-125 cannot be obtained in a single column. The separation efficiency in a single column is limited by the existence of the HFC-125/HFC-32 azeotrope. However, this Comparative Example does show how the azeotrope may be used to substantially separate some fraction of one of the two components from the other in a single column by distilling overhead the azeotrope. Use of azeotropic or azeotrope-like compositions to produce substantially pure HFC-125 and HFC-32 from a starting feed mixture of HFC-125 and HFC-32 is shown in the distillation results of the first and second columns, respectively, where a substantially pure HFC-125 and HFC-32 are obtained as a bottoms stream from the first and second column, respectively. This Comparative Example also shows how to effect a high degree of separation of the two components from a initial HFC-32/HFC-125 feed stream by alternating the operating pressures of the columns such that the composition of the azeotrope and the overhead composition is changed, which in turn alternates which component is in excess relative to the azeotrope, thus allowing each of the components separation and recovery from the other, i.e., demonstrating the use of pressure-swing distillation to separate the two components.

EXAMPLE 11

In this Example, a feed stream consisting of approximately equal weights of HFC-32 and HFC-125 are fed to a first distillation column having 62 stages assumed to operate at 100% efficiency, with the condenser designated as stage 1. The column is 19 inches in diameter. The column is operated at 60 psig, with the condenser operating at −8.1 degrees C., and the reboiler operating at 50.1 degrees C. The feed enters the column at −10 degrees C. and is fed into the column onto stage 38. Methylene chloride from the bottoms of a second column is fed into the first column as an extractant onto stage 12 at −5 degrees C.

The bottoms stream from the first column is then fed to the second distillation column, which has 24 stages assumed to operate at 100% efficiency, with the condenser designated as stage 1. The second column is 23 inches in diameter. The column is operated at 70 psig, with the condenser operating at −9.9 degrees C., and the reboiler operating at 100 degrees C. The feed is fed into the column onto stage 12. The reflux flow in this example is 2000 pph.

The results of this distillation are shown in Table 25.

TABLE 25

First Column Flows in Lbs. Per Hour.

|  | Column Feeds | | Column | Column | Column |
|---|---|---|---|---|---|
|  | Stage 38 | Stage 12 | Reflux | Distillate | Bottoms |
| HFC-125 | 2070.00 | 0.00 | 3997.70 | 2069 | 1.00 |
| HFC-32 | 2070.00 | 0.00 | 0.37 | 0.19 | 2069.81 |
| MeCl2 | 0.00 | 40000.00 | <0.01 | <0.01 | 40000.00 |

Second Column Flows in Lbs. Per Hour

|  | Column Feed | Column Reflux | Column Distillate | Column Bottoms |
|---|---|---|---|---|
| HFC-125 | 1.00 | 1.00 | 1.00 | <0.01 |
| HFC-32 | 2069.81 | 1998.83 | 2069.81 | <0.01 |
| MeCl2 | 40000.00 | <0.01 | <0.01 | 40000.00 | where MeCl2 is methylene chloride.

In this Example, the same high degree separation of both the HFC-125 and HFC-32 which in Comparative Example 11 required two columns is obtained in this Example via a single extractive distillation column. Separating the HFC-32 exiting the bottoms of the first column from the methylene chloride extractant is easily effected by the second distillation. Combined, the pair of columns in this Example required to obtain the two separate and high purity HFC-125 and HFC-32 product streams from the initial HFC-125/HFC-32 fresh feed stream have significantly smaller diameters, fewer stages, and lower reflux flows than the pair of columns required in Comparative Example 11. Compared to Comparative Example 11, this translates into significantly lower investment and energy costs to effect the separation.

The aforementioned invention as illustrated by the above Examples may be practiced on any stream containing the subject components produced by any method. However, the distillation processes described above are particularly advantageous for removing CFC-115 from HFC-125 and HFC-32 that have been co-produced. For example, simultaneously feeding methylene chloride (HCC-30), HCFC-124 (chlorotetrafluoroethane) and hydrogen fluoride (HF), or imultaneously feeding methylene chloride, HCFC-123 (dichlorotetrafluoroethane) and hydrogen fluoride (HF), in a vapor phase at a range of temperatures and feed ratios over suitable chrome-containing catalysts can produce an off-gas stream comprising HFC-32, HFC-125 and CFC-115. Other reaction off-gas components, e.g., methylene chloride (HCC-30), HCFC-31 (chlorofluoromethane), HCFC-123, HCFC-124, HCl, among others may separated by any conventional means, e.g., by distillation, and, in the case of methylene chloride, HCFC-31, HCFC-123, HCFC-124 may be recycled back to the reactor.

The residual acidity can, if desired, be removed by any suitable methods, e.g., by washing with water then drying with molecular sieves. The azeotrope distillation described above may then be employed to reduce the CFC-115 content.

Suitable catalysts include those described in U.S. Pat. Nos. 4,155,881 or 5,334,787, or copending and commonly assigned U.S. patent application Ser. No. 08/146,334 (Attorney Docket No. CR-9436); the disclosure of which has been incorporated by reference. Other catalysts and fluorination processes for co-producing HFC-125 and HFC-32 are also suitable for the practice of this invention.

The following examples illustrate the results obtained by co-feeding precursors of HFC-32 and HFC-125 with HF in a catalytic reactor under a variety of reaction conditions:

EXAMPLE 12

The catalyst of U.S. Pat. No. 5,334,787, hereby incorporated by reference, was prepared and pre-treated with hydrogen fluoride (HF) as disclosed in that patent. Mixtures comprising hydrogen fluoride, methylene chloride, and HCFC-124 were fed over the catalyst at atmospheric pressure, at the temperature and contact time listed below in Table 26, and with results as noted:

TABLE 26

Organic Mole % HFC-32, HFC-125, CFC-115 vs. Operating Condition

| Contact Time (Sec) | HF/Tot. Org. in Feed (Mole Ratio) | HF/HCC-30 in Feed (Mole Ratio) | HF/HCFC-124 in Feed (Mole Ratio) | Temp (deg. C.) | Mole % 32 | Mole % 125 | Mole % 115 |
|---|---|---|---|---|---|---|---|
| 10 | 3.1 | 4.8 | 8.5 | 301 | 32.1 | 12.4 | <0.05 |
| 10 | 3.1 | 7.2 | 5.4 | 301 | 25.1 | 21.2 | 0.1 |
| 31 | 3.4 | 4.9 | 11.0 | 301 | 32.1 | 15.8 | 0.2 |
| 31 | 3.4 | 7.3 | 6.4 | 301 | 29.8 | 13.4 | 0.1 |
| 10 | 6.5 | 9.9 | 18.6 | 301 | 43.8 | 13.9 | <0.05 |
| 10 | 6.4 | 14.3 | 11.5 | 301 | 31.7 | 21.6 | <0.05 |
| 30 | 6.5 | 8.3 | 30.3 | 301 | 48.9 | 17.6 | 0.1 |
| 31 | 8.0 | 16.6 | 15.5 | 301 | 39.3 | 27.5 | 0.2 |
| 20 | 4.7 | 7.9 | 11.8 | 301 | 36.0 | 21.5 | 0.1 |
| 20 | 5.0 | 8.6 | 11.8 | 327 | 42.8 | 17.4 | 0.2 |
| 20 | 4.7 | 7.9 | 11.8 | 327 | 30.0 | 37.4 | 0.3 |
| 20 | 4.8 | 6.8 | 15.7 | 327 | 34.8 | 33.4 | 0.3 |
| 20 | 5.3 | 11.9 | 9.4 | 327 | 25.6 | 50.0 | 0.4 |
| 10 | 4.7 | 8.6 | 10.3 | 327 | 32.8 | 31.4 | 0.2 |
| 30 | 5.0 | 8.0 | 13.6 | 327 | 51.0 | 20.9 | 0.5 |
| 20 | 3.1 | 5.5 | 7.3 | 327 | 24.0 | 32.5 | 0.4 |
| 20 | 7.2 | 12.4 | 17.0 | 327 | 34.2 | 29.0 | 0.3 |
| 20 | 4.7 | 7.9 | 11.8 | 327 | 33.7 | 27.5 | 0.3 |
| 10 | 3.1 | 4.8 | 8.5 | 351 | 26.8 | 27.9 | 0.6 |
| 10 | 3.1 | 7.2 | 5.4 | 351 | 18.8 | 44.3 | 0.7 |
| 31 | 3.4 | 4.9 | 11.0 | 351 | 26.0 | 14.8 | 0.9 |
| 31 | 3.4 | 7.3 | 6.4 | 351 | 20.5 | 44.0 | 1.5 |

TABLE 26-continued

Organic Mole % HFC-32, HFC-125, CFC-115 vs. Operating Condition

| Contact Time (Sec) | HF/Tot. Org. in Feed (Mole Ratio) | HF/HCC-30 in Feed (Mole Ratio) | HF/HCFC-124 in Feed (Mole Ratio) | Temp (deg. C.) | Mole % 32 | Mole % 125 | Mole % 115 |
|---|---|---|---|---|---|---|---|
| 10 | 6.5 | 9.9 | 18.6 | 351 | 38.8 | 31.8 | 0.3 |
| 10 | 6.4 | 14.3 | 11.5 | 351 | 25.8 | 50.6 | 0.4 |

Where:
"Contact Time" is the contact time in the reactor, in seconds.
"Temp" is the temperature the reaction is being run, in degrees C.
"HF/Tot. Org." is the HF/Total Organic molar feed ratio to the reactor.
"HF/HCC-30" is the HF/HCC-30 molar feed ratio to the reactor.
"HF/HCFC-124" is the HF/HCFC-124 molar feed ratio to the reactor.
"% 32" is the organic mole % HFC-32 in the reactor off-gas.
"% 125" is the organic mole % HFC-125 in the reactor off-gas.
"% 115" is the organic mole % CFC-115 in the reactor off-gas.

This Example shows how a variety of HFC-32 and HFC-125 molar ratios and productivities may be obtained by adjusting feed ratios and operating conditions.

EXAMPLE 13

The catalyst described in U.S. patent application Ser. No. 08/146,334 (Attorney Docket No. CR-9436) was prepared and pre-treated with hydrogen fluoride (HF) as disclosed in that patent application. Mixtures comprising hydrogen fluoride, methylene chloride, and HCFC-124 were fed over the catalyst at atmospheric pressure, at the temperature and contact time listed below in Table 27, and with results as noted in Table 27:

TABLE 27

Organic Mole % HFC-32, HFC-125 vs. Operating Conditions

| Contact Time (sec) | Temp (deg. C.) | HF/Tot. Org. | % HCC-30 | % HFC-32 | % HFC-125 |
|---|---|---|---|---|---|
| 26 | 327 | 5.2 | 58 | 40 | 27 |
| 12 | 304 | 3.4 | 64 | 38 | 20 |
| 12 | 302 | 3.4 | 42 | 24 | 24 |
| 12 | 302 | 7.2 | 66 | 47 | 18 |
| 12 | 302 | 7.2 | 44 | 31 | 32 |
| 26 | 302 | 5.2 | 58 | 32 | 18 |
| 27 | 329 | 5.2 | 58 | 40 | 27 |
| 26 | 327 | 5.3 | 69 | 49 | 24 |
| 26 | 327 | 4.9 | 51 | 36 | 35 |

Where:
"Contact Time" is the contact time in the reactor, in seconds.
"Temp" is the temperature the reaction is being run, in degrees C.
"HF/Tot. Org" is the HF/Total Organic molar feed ratio to the reactor.
"% HCC-30" is the organic mole % HCC-30 in the feed stream to the reactor.
"% HFC-32" is the organic mole % HFC-32 in the reactor off-gas.
"% HFC-125" is the organic mole % HFC-125 in the reactor off-gas.

This Example shows how a variety of HFC-32 and HFC-125 molar ratios and productivities may be obtained by adjusting feed ratios and operating conditions.

In general, this chemistry as shown in Example 12 and Example 13 may be operated at temperatures that range from about 175 to 400 degrees C.; normally from about 250 to 350 degrees C. This chemistry may also be operated by employing an HF/total organic molar feed ratio of from about 2/1 to 10/1; normally from about 4/1 to 8/1, and may be operated from atmospheric pressure up to 200 psig. The chemistry may be used to obtain off-gas compositions containing from about 5 to 70 organic mole % HFC-125 and from 5 to 70 organic mole % HFC-32. The catalyst of Example 13 is desirable for this chemistry because the catalyst of Example 13 is particularly resistant to deactivation in this chemistry, and the catalyst of Example 13 can subsequently be regenerated after any activity loss. The catalyst of Example 13 may be reactivated, regaining its initial, or, in some cases, obtaining greater than its initial activity, by, for example, using the procedure described in U.S. Pat. No. 4,155,881, the disclosure of which is hereby incorporated by reference.

We claim:

1. A process for separating HFC-32 and HFC-125 from a first mixture by using an extractant comprising methylene chloride, the process comprising the steps of: adding the extractant to the first mixture in order to form a second mixture, separating HFC-32 and HFC-125 in the second mixture by extractively distilling the second mixture in an extractive distillation zone of a distillation column and thereby recovering HFC-125 as an overhead product of the column and HFC-32 from the column bottom.

* * * * *